United States Patent
Lim et al.

(10) Patent No.: US 11,940,620 B2
(45) Date of Patent: Mar. 26, 2024

(54) METHOD OF CLEANING COLLECTOR OF EUV LIGHT SOURCE SYSTEM

(71) Applicant: Samsung Electronics Co., Ltd., Suwon-si (KR)

(72) Inventors: Changsoon Lim, Hwaseong-si (KR); Youngdo Kim, Hwaseong-si (KR); Daewon Kang, Seoul (KR); Chansoo Kang, Hwaseong-si (KR); Hoonseop Kim, Suwon-si (KR); Sangki Nam, Seongnam-si (KR); Youngduk Suh, Seoul (KR); Donghyub Lee, Hwaseong-si (KR); Jonghun Pi, Gunwi-gun (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 118 days.

(21) Appl. No.: 17/508,224

(22) Filed: Oct. 22, 2021

(65) Prior Publication Data

US 2022/0308339 A1    Sep. 29, 2022

(30) Foreign Application Priority Data

Mar. 23, 2021 (KR) .......................... 10-2021-0037580

(51) Int. Cl.
*G02B 27/00* (2006.01)
*B08B 7/00* (2006.01)
(Continued)

(52) U.S. Cl.
CPC ........ *G02B 27/0006* (2013.01); *B08B 7/0035* (2013.01); *B08B 7/04* (2013.01);
(Continued)

(58) Field of Classification Search
CPC ..... G02B 27/0006; B08B 7/0035; B08B 7/04; B08B 7/0092; B08B 13/00;
(Continued)

(56) References Cited

U.S. PATENT DOCUMENTS 8,953,145 B2    2/2015   Kraus et al.
9,810,991 B2    11/2017  Chilese et al.
(Continued)

FOREIGN PATENT DOCUMENTS

KR    2016-0134648 A   11/2016
KR    2019-0034257 A    4/2019
(Continued)

*Primary Examiner* — Erin F Bergner
(74) *Attorney, Agent, or Firm* — Harness, Dickey & Pierce, P.L.C.

(57) ABSTRACT

A method of cleaning a collector of an extreme ultraviolet light source system includes introducing the collector separated from the extreme ultraviolet light source system into a chamber; capturing an optical image of a reflective surface of the collector; measuring a contamination level of the reflective surface by comparing the optical image with a prestored standard image; performing a first cleaning operation if the contamination level exceeds a preset first reference value, the first cleaning operation including cleaning the reflective surface by spraying dry ice particles onto the reflective surface; and performing a second cleaning operation if the contamination level is less than or equal to the preset first reference value. The second cleaning operation includes cleaning the reflective surface by radiating atmospheric plasma onto the reflective surface and measuring a microcontamination level and a damage level of the reflective surface.

20 Claims, 7 Drawing Sheets

(51) Int. Cl.
*B08B 7/04* (2006.01)
*G01N 33/00* (2006.01)
*G03F 7/00* (2006.01)
*G06T 7/00* (2017.01)

(52) U.S. Cl.
CPC ..... *G01N 33/0027* (2013.01); *G03F 7/70033* (2013.01); *G03F 7/7085* (2013.01); *G03F 7/70925* (2013.01); *G06T 7/001* (2013.01)

(58) Field of Classification Search
CPC ............ G01N 33/0027; G03F 7/70033; G03F 7/7085; G03F 7/70925; G03F 7/70175; G03F 7/70591; G03F 7/70975; G06T 7/001; B24C 1/003
See application file for complete search history.

(56) References Cited

U.S. PATENT DOCUMENTS

| | | | |
|---|---|---|---|
| 10,245,623 | B2 | 4/2019 | Swanson et al. |
| 2007/0069162 | A1* | 3/2007 | Banine .................... G03B 7/20 250/504 R |
| 2008/0151201 | A1* | 6/2008 | Storm ................. G03F 7/70058 355/30 |
| 2009/0301517 | A1* | 12/2009 | Asayama ................ B08B 13/00 134/1.1 |
| 2010/0288302 | A1 | 11/2010 | Ehm et al. |
| 2011/0048452 | A1* | 3/2011 | Zink ........................ B08B 7/00 134/1 |
| 2012/0298134 | A1 | 11/2012 | Moriya et al. |
| 2013/0319466 | A1 | 12/2013 | Mizoguchi et al. |
| 2015/0266067 | A1 | 9/2015 | Ershov |
| 2016/0062251 | A1* | 3/2016 | Machida ................. H05G 2/005 359/507 |
| 2018/0259861 | A1 | 9/2018 | Langlois |
| 2019/0302628 | A1* | 10/2019 | Meier ................. G03F 7/70316 |

FOREIGN PATENT DOCUMENTS

| | | |
|---|---|---|
| KR | 2019-0122812 A | 10/2019 |
| KR | 2020-0031499 A | 3/2020 |
| KR | 2020-0074957 A | 6/2020 |
| WO | WO-2018-019494 A1 | 2/2018 |
| WO | WO-2019-091708 A1 | 5/2019 |

* cited by examiner

METHOD OF CLEANING COLLECTOR OF EUV LIGHT SOURCE SYSTEM

CROSS-REFERENCE TO RELATED APPLICATION(S)

This application claims the benefit under 35 USC 119(a) of Korean Patent Application No. 10-2021-0037580, filed on Mar. 23, 2021 in the Korean Intellectual Property Office, the entire disclosure of which is incorporated herein by reference for all purposes.

BACKGROUND

The present disclosure relates to a method of cleaning a collector of an extreme ultraviolet light source system.

Collectors of an extreme ultraviolet (EUV) source system reflect and concentrate extreme ultraviolet light emitted from source materials and transmit the concentrated light to exposure systems, for example, scanner systems. When a collector is contaminated, the output of an extreme ultraviolet light source system may deteriorate, which may be a factor in lowering operating performance of extreme ultraviolet exposure equipment. Therefore, contaminants adhering to the surface of a collector may need to be cleaned after a desired and/or alternatively predetermined operating time has elapsed.

SUMMARY

Example embodiments provide a method of cleaning a collector of an extreme ultraviolet light source system, in which contaminants attached to a surface of the collector may be effectively cleaned.

According to example embodiments, a method of cleaning a collector of an extreme ultraviolet light source system includes introducing the collector, separated from the extreme ultraviolet light source system, into a chamber; capturing an optical image of a reflective surface of the collector; measuring a contamination level of the reflective surface by comparing the optical image with a prestored standard image; performing a first cleaning process if the contamination level exceeds a preset first reference value, the first cleaning process including cleaning the reflective surface by spraying dry ice particles onto the reflective surface, and performing a second cleaning process if the contamination level is less than or equal to the preset first reference value. The second cleaning process includes cleaning the reflective surface by radiating atmospheric plasma onto the reflective surface. The second cleaning process includes measuring a microcontamination level and a damage level of the reflective surface, generating a microcontamination level map of the reflective surface and a damage level map of the reflective surface, based on the microcontamination level and the damage level, and cleaning by radiating the atmospheric plasma onto an area of the reflective surface in which the microcontamination level and the damage level exceed a preset second reference value and a present third reference value, respectively, based on the microcontamination level map and the damage level map.

According to example embodiments, a method of cleaning a collector of an extreme ultraviolet light source system includes inputting the collector separated from the extreme ultraviolet light source system into a chamber; capturing an optical image of a reflective surface of the collector; measuring a contamination level of the reflective surface by comparing the optical image with a pre-stored standard image; performing a first cleaning operation if the contamination level exceeds a preset first reference value, the first cleaning operation including cleaning the reflective surface by spraying dry ice particles onto the reflective surface; performing a second cleaning operation if the contamination level is less than or equal to the preset reference value. The second cleaning operation includes cleaning the reflective surface by radiating atmospheric plasma onto the reflective surface and measuring a microcontamination level and a damage level of the reflective surface.

According to example embodiments, a method of cleaning a collector of an extreme ultraviolet light source system includes introducing the collector, separated from the extreme ultraviolet light source system, into a chamber; capturing an optical image of a reflective surface of the collector using a first measuring device; measuring a contamination level of the reflective surface by comparing the optical image with a pre-stored standard image; performing a first cleaning operation if the contamination level exceeds a preset first reference value, the first cleaning operation including physically cleaning the reflective surface by spraying dry ice particles onto the reflective surface using a first cleaning apparatus; and performing a second cleaning operation if the contamination level is less than or equal to the preset first reference value, the second cleaning operation including chemically cleaning the reflective surface by radiating atmospheric plasma onto the reflective surface using a second cleaning apparatus and measuring a microcontamination level of the reflective surface and a damage level of the reflective surface using a second measuring device.

BRIEF DESCRIPTION OF DRAWINGS

The above and other aspects, features, and advantages of inventive concepts will be more clearly understood from the following detailed description, taken in conjunction with the accompanying drawings, in which.

DETAILED DESCRIPTION

Hereinafter, various embodiments will be described in detail with reference to the accompanying drawings.

Figure 1:
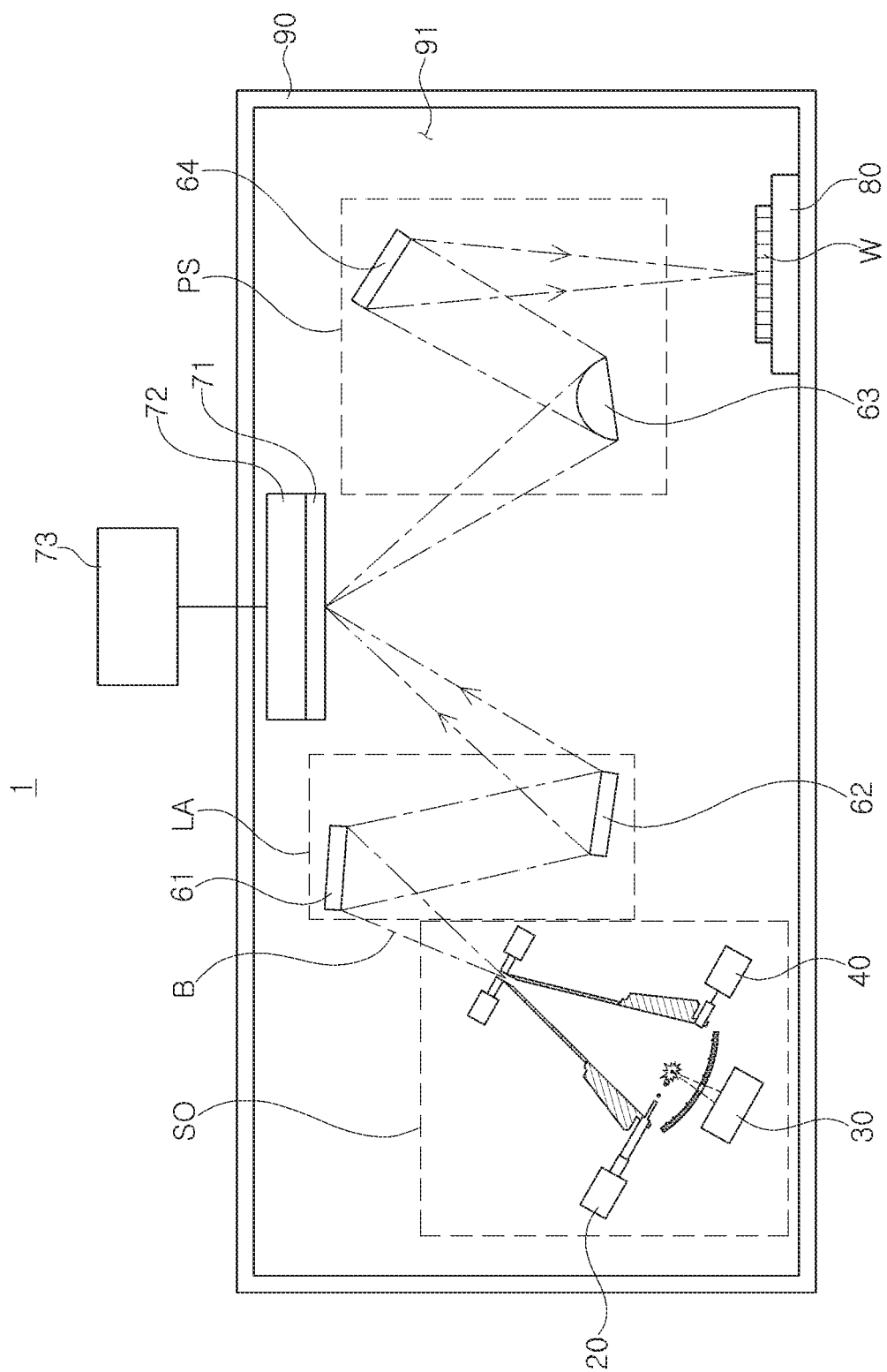
FIG. 1 is a diagram schematically illustrating an extreme ultraviolet exposure facility employing an extreme ultraviolet light source system.
Figure 2:
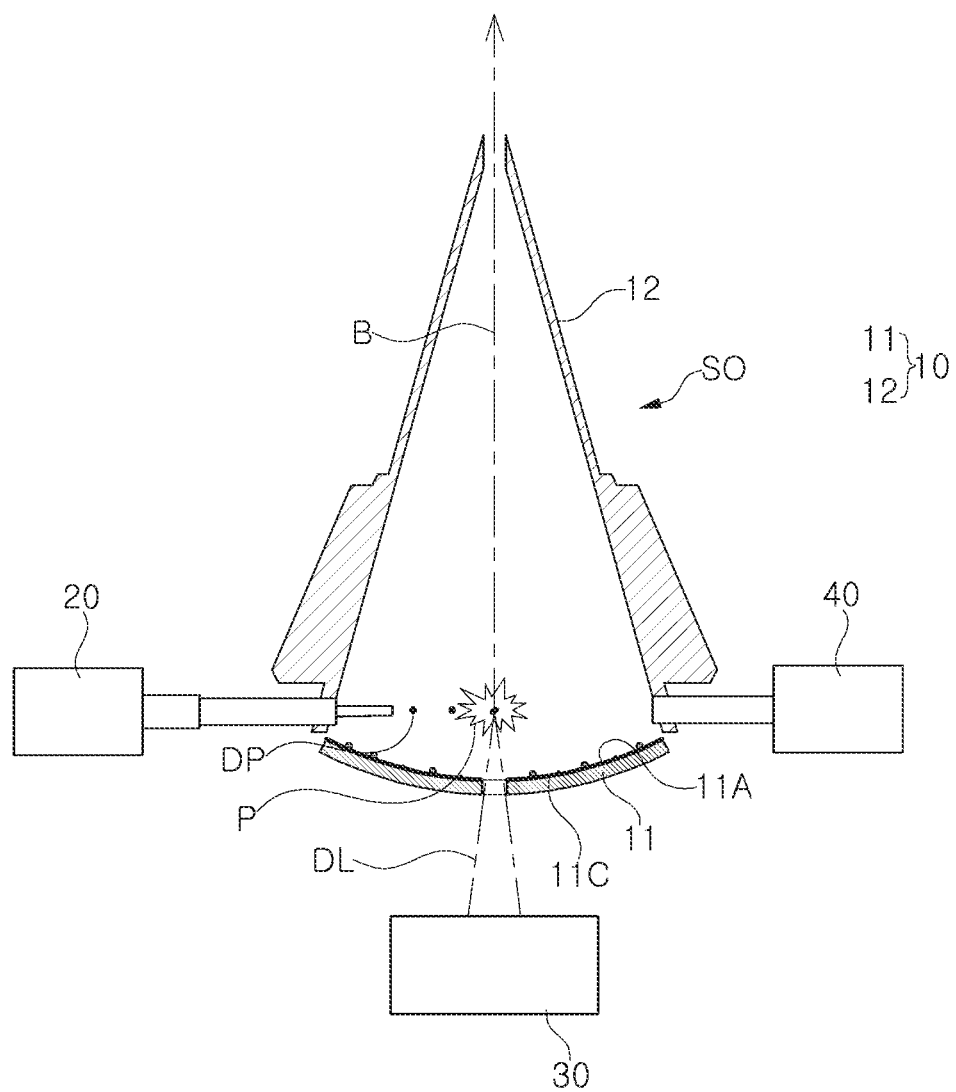
FIG. 2 is a diagram schematically illustrating the extreme ultraviolet light source system of FIG. 1.

Referring to FIGS. 1 and 2, an extreme ultraviolet light source system and an extreme ultraviolet exposure facility in which a collector to be cleaned by a collector cleaning apparatus according to an embodiment is employed will be described. FIG. 1 is a diagram schematically illustrating an extreme ultraviolet exposure facility employing an extreme ultraviolet light source system, and FIG. 2 is a diagram schematically illustrating the extreme ultraviolet light source system of FIG. 1.

Referring to FIG. 1, an extreme ultraviolet exposure facility 1 may include an exposure chamber 90, an extreme ultraviolet light source system SO, a lithographic apparatus LA, a projection system PS, an upper electrostatic chuck (ESC) 72, and a lower electrostatic chuck 80.

The exposure chamber 90 has an internal space 91, in which the extreme ultraviolet light source system SO, the lithographic apparatus LA, the projection system PS, the upper electrostatic chuck 72 and the lower electrostatic chuck 80 may be located. A mask 71 may be loaded/unloaded on/from the upper electrostatic chuck 72 by electrostatic force generated by power applied from a power supply 73, and a substrate W such as a semiconductor wafer may be loaded/unloaded on/from the lower electrostatic chuck 80.

Referring to FIG. 2, the extreme ultraviolet light source system SO may generate extreme ultraviolet light B having a wavelength of less than about 100 nm. The extreme ultraviolet light source system SO may be a laser-produced plasma (LPP) light source generating plasma by irradiating laser light DL oscillated from a light source unit 30 to a droplet formed of any one of tin (Sn), lithium (Li), and xenon (Xe). In addition, the extreme ultraviolet light source system SO may use a so-called Master Oscillator Power Amplifier (MOPA) method. For example, by using a seed laser irradiated from the light source unit 30, a pre-pulse and a main pulse are generated, and the pre-pulse is irradiated to expand the droplets, and then the main pulse is re-irradiated to the droplets (DP), thereby generating plasma P and emitting extreme ultraviolet light (B) using the plasma (P). Residues of the droplets DP remaining after being irradiated with the main pulse may be accommodated in a catcher 40 (e.g., container with housing).

Inside a light source chamber 10 of the extreme ultraviolet light source system SO, the laser light DL supplied by the light source unit 30 and the droplets supplied by a droplet supply unit 20 collide 50000 or more times per second, and thus, the plasma (P) may be generated. The collector 11 of the light source chamber 10 may collect the extreme ultraviolet light B emitted in all directions from the plasma P, focus the collected light forward, and provide the light to the lithographic apparatus LA. The light source chamber 10 may include a collector 11 for condensing the generated extreme ultraviolet light B, and an upper body 12 coupled to the collector 11 and having a conical outer shape. The inside of the light source chamber 10 may be maintained in an ultra-low pressure state to limit and/or prevent the generated extreme ultraviolet light B from being absorbed by the gas inside the light source chamber 10. A reflective layer 11C for improving reflectivity of the extreme ultraviolet light B may be formed on a reflective surface 11A of the collector 11. The reflective layer 11C may be formed of a multi-thin layer in which molybdenum and silicon (Mo—Si) are alternately stacked or of a material such as zirconium.

The lithographic apparatus LA may include a plurality of mirrors to irradiate the extreme ultraviolet light B emitted from the extreme ultraviolet light source system SO toward the upper electrostatic chuck 72. Since a plurality of mirrors included in the lithographic apparatus LA may have a known structure, only two mirrors 61 and 62 are illustrated for simplification of the drawing and convenience of description.

The projection system PS includes a plurality of mirrors to project the pattern of extreme ultraviolet light B reflected from the mask 71 attached to the upper electrostatic chuck 72 to the substrate W disposed on the lower electrostatic chuck 80, to expose the pattern on the surface of the substrate W. Since a number of mirrors included in the projection system PS may have a known structure, only two mirrors 63 and 64 are illustrated for simplicity of drawing and convenience of explanation.

A cleaning apparatus according to an example embodiment of inventive concepts may be used in the process of cleaning the collector 11 of the extreme ultraviolet light source system SO. Hereinafter, a cleaning apparatus 100 according to an example embodiment will be described with reference to FIG. 3.

Figure 3:
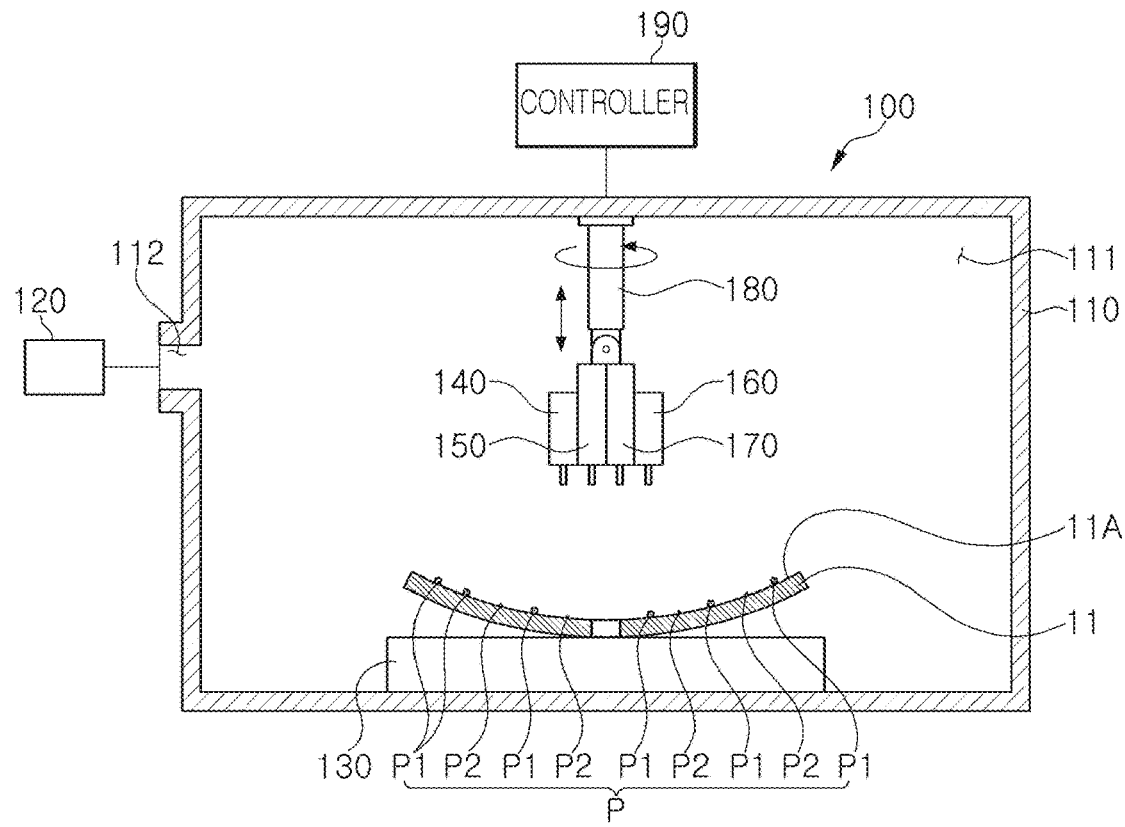
FIG. 3 is a side cross-sectional view schematically illustrating an apparatus for cleaning a collector of an extreme ultraviolet light source system according to an example embodiment.

Referring to FIG. 3, the cleaning apparatus 100 according to an example embodiment may include a cleaning chamber 110, a support 130 disposed inside of the cleaning chamber 110 to support a collector 11 described above, first and second measuring devices 140 and 160 disposed above the support 130, first and second cleaning apparatuses 150 and 170, and an inlet 112 into which process gas provided from a gas supply source 120 may be introduced. Respective components constituting the cleaning apparatus 100 may be controlled by a controller 190.

The controller 190 controls the overall operation of the cleaning apparatus 100, and for example, may be implemented as a processor, such as a central processing unit (CPU), a graphics processing unit (GPU), a microprocessor, an application specific integrated circuit (ASIC), Field Programmable Gate Arrays (FPGA), or the like, and may include a memory for storing various data required for the operation of the cleaning apparatus 100.

The first and second measuring devices 140 and 160 and the first and second cleaning apparatuses 150 and 170 are disposed on one end of an arm 180, and may move along the reflective surface 11A of the collector 11 according to the rotation of the arm 180. In addition, the first and second measuring devices 140 and 160 and the first and second cleaning apparatuses 150 and 170 are raised and lowered by the arm 180 to be spaced apart from or to be adjacent to the reflective surface 11A of the collector 11.

The cleaning chamber 110 has an internal space 111 in which a cleaning process for cleaning the collector 11 is performed, and may be formed of a material having excellent wear resistance and corrosion resistance. The internal space 111 is filled with process gas to maintain atmospheric pressure, which may be used for generating atmospheric plasma in the internal space 111. In an example embodiment, the first and second measuring devices 140 and 160 and the first and second cleaning apparatuses 150 and 170 are all disposed in one cleaning chamber 110 as an example, but a plurality of chambers may also be employed. For example, the first measuring device 140 and the first cleaning apparatus 150 may be disposed in a first cleaning chamber, and the second measuring device 160 and the second cleaning apparatus 170 may be disposed in a second cleaning chamber.

The first measuring device 140 may generate an optical image by capturing an image of the reflective surface 11A. The first measuring device 140 may be a camera employing an image sensor such as a CCD sensor or a CMOS sensor. The optical image is for roughly measuring the level of contamination of the reflective surface 11A, and may be generated by the first measuring device 140 and transmitted to the controller 190. The controller 190 may calculate a contamination level of the reflective surface 11A by comparing the transmitted optical image with a preset standard image. For example, the standard image may be an optical image obtained by imaging that the reflective surface 11A is totally contaminated. The controller 190 may calculate the contamination level of the captured optical image by considering the contamination level of the standard image as 100%. Also, when (or if, or in response to) the calculated contamination level exceeds a preset reference value (and/or present threshold value), the controller 190 may perform a first cleaning process of physically cleaning the reflective surface 11A. Also, when (or if, or in response to) the calculated contamination level is less than or equal to a preset reference value (and/or preset threshold value), the controller 190 may perform a second cleaning process of chemically cleaning the reflective surface 11A.

The first cleaning process may be performed by the first cleaning apparatus 150, and the second cleaning process may be performed by the second cleaning apparatus 170.

The first cleaning apparatus 150 is for removing contaminants P1 having relatively large particles among contaminants P1 and P2 attached to the reflective surface 11A. The first cleaning apparatus 150 may perform so-called $CO_2$ snow cleaning, in which high-speed dry ice particles S are sprayed on the reflective surface 11A for several hours to several tens of hours. The dry ice particles S sprayed on the reflective surface 11A may instantaneously expand the contaminants attached to the reflective surface 11A to separate the contaminants P1 from the reflective surface 11A. The first cleaning apparatus 150 may include a nozzle for spraying the dry ice particles.

The second measuring device 160 is for precisely measuring the level of contamination of the reflective surface 11A. The second measuring device 160 may measure a microcontamination level, which is a contamination level lower than the contamination level previously measured by the first measuring device 140. For example, the second measuring device 160 may be a measuring device for detecting chemical species emitted from the reflective surface 11A by atmospheric plasma radiated to the reflective surface 11A. As the second measuring device 160, an optical emission spectrometer, an optical absorption spectrometer, or a laser induced fluorescence detector may be employed. In addition, a gas detector may be additionally employed on the second measuring device 160 as an auxiliary. The second measuring device 160 moves to be adjacent to the reflective surface 11A and then moves along the reflective surface 11A to detect a chemical species from the reflective surface 11A. Therefore, the surface state of the reflective surface 11A may be measured. For example, a region in which a chemical species of a material included in a droplet is detected by the second measuring device 160 may be regarded as a region to which contaminants are attached. Also, a region in which a chemical species of a material constituting the reflective layer 11C is detected by the second measuring device 160 may be regarded as being an uncontaminated region. In addition, when the second measuring device 160 (e.g., image sensor circuit) detects a material not included in a droplet and the reflective layer 11C, for example, a chemical species of a material constituting the collector body disposed below the reflective layer 11C, it may be regarded that the reflective layer 11C is damaged.

The second cleaning apparatus 170 may be an atmospheric plasma cleaning apparatus in which atmospheric plasma cleaning is performed. Accordingly, in a state in which the internal space 111 of the cleaning chamber 110 is maintained at atmospheric pressure, atmospheric plasma is radiated to the reflective surface 11A to clean the reflective surface 11A. The second cleaning apparatus 170 may include a plasma jet.

Figure 4:
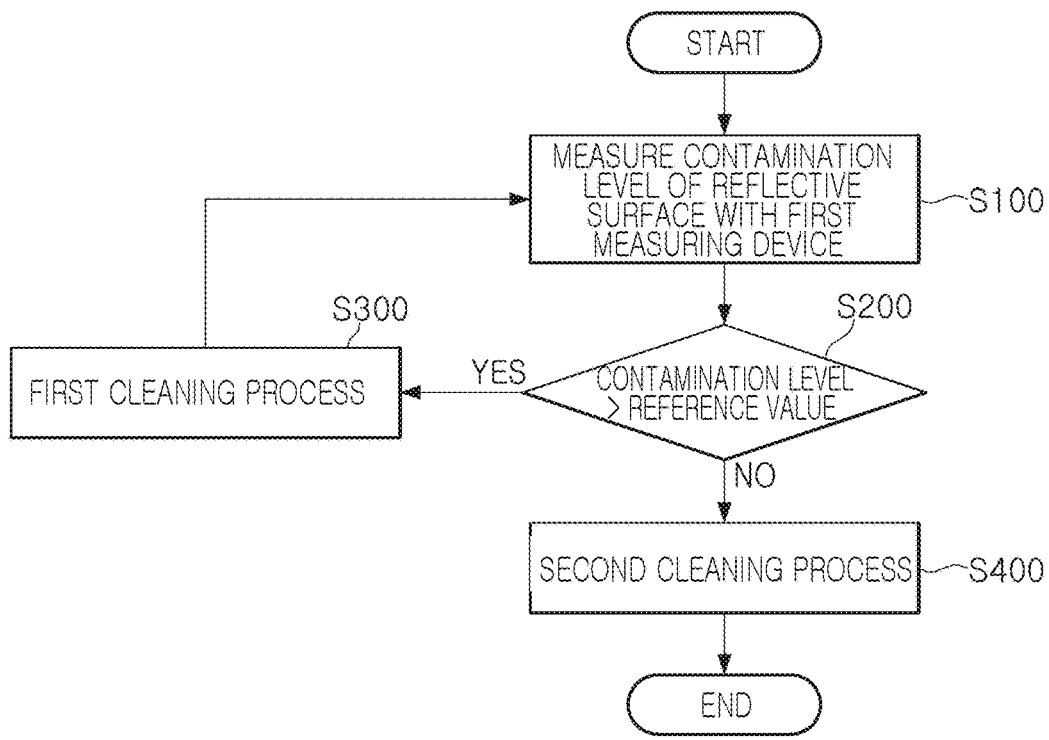
FIG. 4 is a flowchart of a method of cleaning a collector of an extreme ultraviolet light source system according to an example embodiment.
Figure 5:
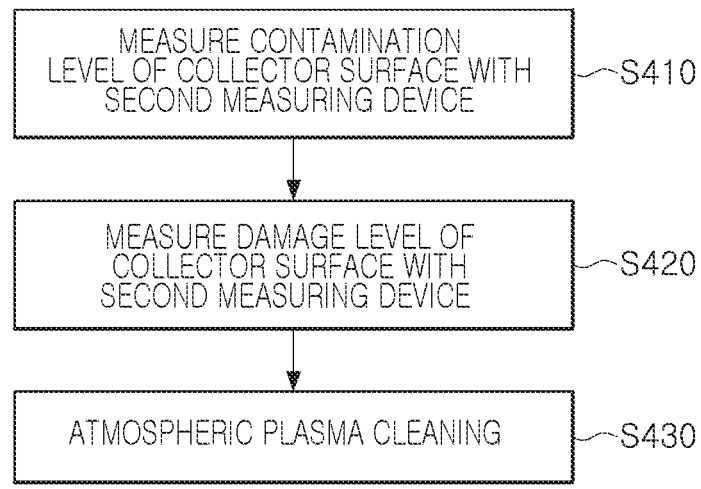
FIG. 5 is a detailed flowchart of a second cleaning process of FIG. 4.

Next, referring to FIGS. 4 to 9, a method of cleaning a collector of an extreme ultraviolet light source system according to an example embodiment will be described. FIG. 4 is a flowchart illustrating a method of cleaning a collector of an extreme ultraviolet light source system according to an example embodiment, FIG. 5 is a detailed flowchart of a second cleaning process of FIG. 4. FIGS. 6 to 9 are views illustrating a method of cleaning a collector of an extreme ultraviolet light source system according to an example embodiment. Among the reference numbers of FIGS. 6 to 9, the same reference numerals as those of FIG. 3 described above may be understood to have the same configuration.

Figure 6:
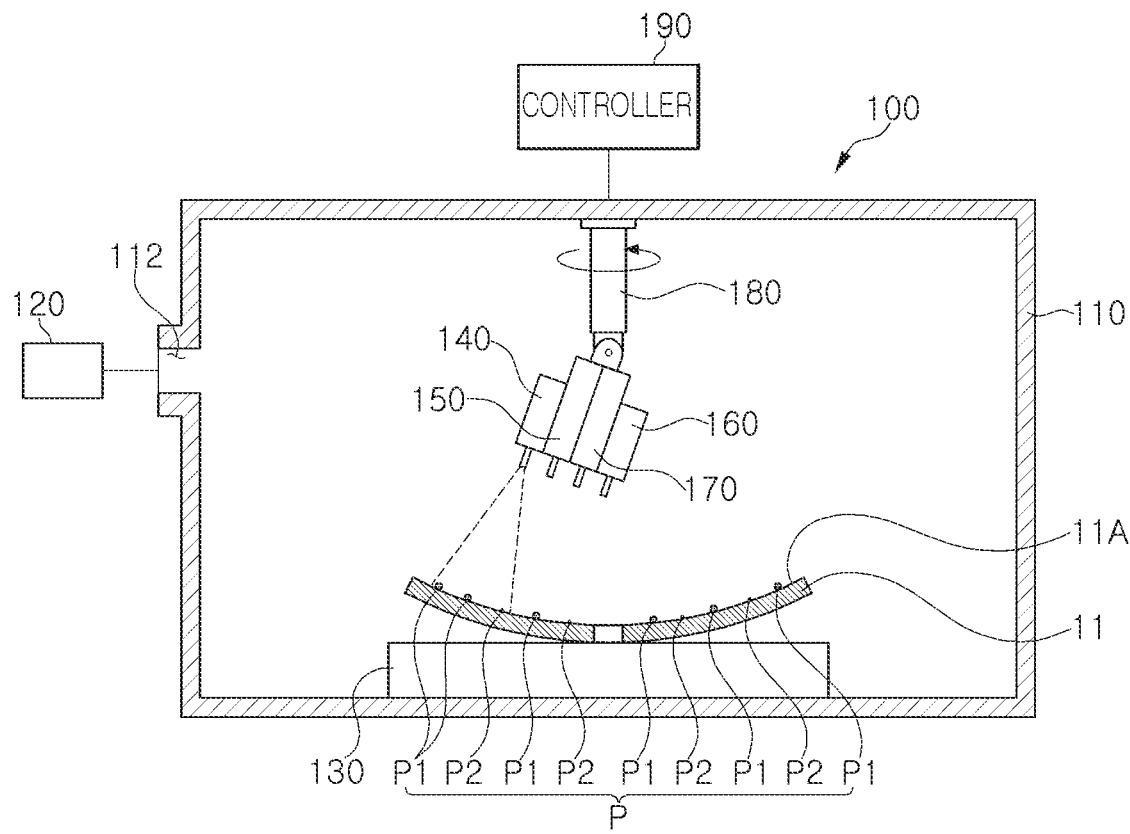
FIGS. 6 to 9 are views illustrating a method of cleaning a collector of an extreme ultraviolet light source system according to an example embodiment.

Referring to FIGS. 4 and 6, the collector 11 may be separated from the extreme ultraviolet light source system and disposed on the support 130 in the cleaning chamber 110, and an operation of measuring a contamination level of the reflective surface 11A of the collector 11 may be performed (S100). The contamination level of the reflective surface 11A may be measured through the first measuring device 140.

The first measuring device 140 may capture an optical image of the reflective surface 11A of the collector 11 and transmit the captured image to the controller 190. The controller 190 may calculate the overall contamination level of the reflective surface 11A by comparing the transmitted image with a standard image stored in advance. For example, the standard image is an optical image obtained by imaging that the reflective surface 11A is totally contaminated, and may be pre-stored in the controller 190. The first measuring device 140 may generate one image by capturing an image of the entire reflective surface 11A of the collector 11 once. In addition, the first measuring device 140 may also divide the reflective surface 11A of the collector 11 into a plurality of regions, generates images of the respective regions, and then merges the images into one image, and transmit the merged image to the controller 190.

Next, the measured contamination level is compared with a preset reference value, and one of first and second cleaning processes may be performed according to the comparison result (S200). The controller 190 may calculate the contamination level of the captured optical image by considering the contamination level of the standard image as 100%. The controller 190 may perform the first cleaning process when the calculated contamination level exceeds the reference value, and may perform the second cleaning process when the calculated contamination level is less than or equal to the reference value. In an example embodiment, when the captured optical image exceeds 10% of the contamination level of the standard image, the controller 190 determines that the reflective surface 11A is relatively heavily contaminated and performs the first cleaning process. In addition, when the captured optical image is 10% or less of the contamination level of the standard image, the controller 190 may determine that the reflective surface 11A is relatively less contaminated and perform a second cleaning process. Such a reference value may be determined in consideration of the overall size and weight of contaminants P1 and P2 attached to the reflective surface 11A.

Figure 7:
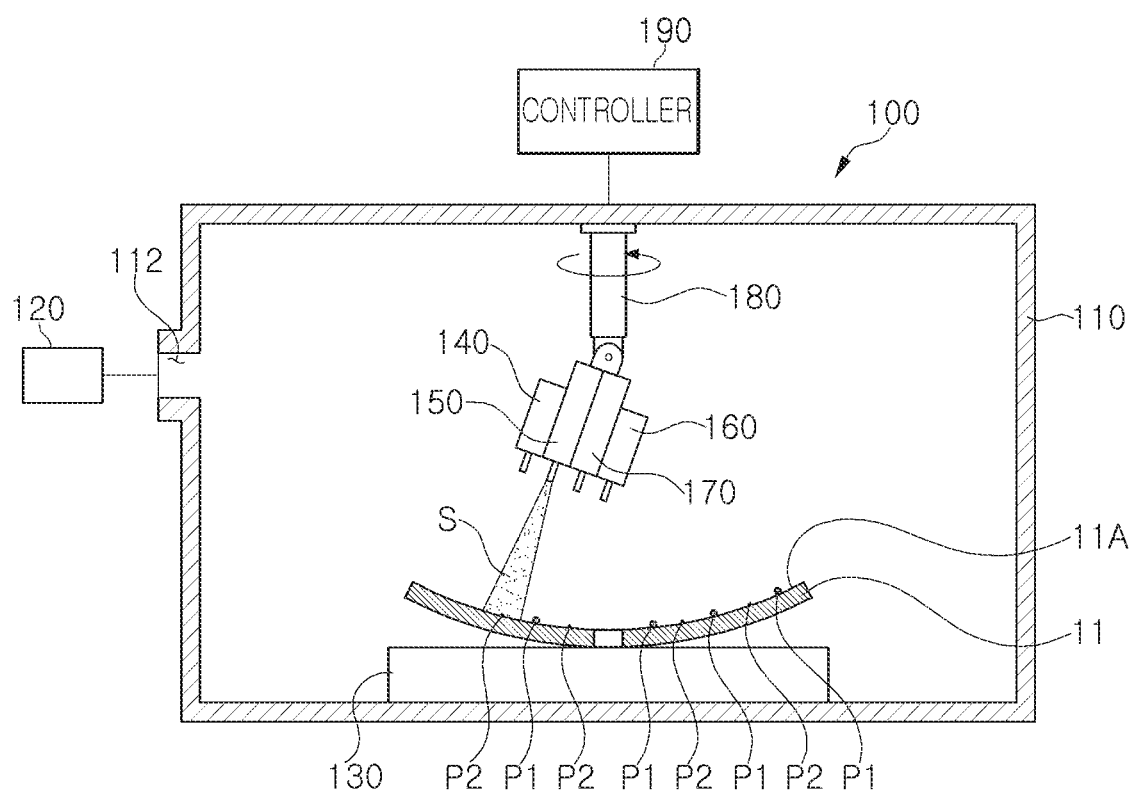

Referring to FIGS. 4 and 7, a first cleaning process (S300) may be performed when the reflective surface 11A is relatively heavily contaminated. The first cleaning process S300 is a process for first removing the large contaminants P1 attached to the reflective surface 11A, and physical cleaning may be performed in the first process S300. As the physical cleaning, for example, the first cleaning process may be performed by spraying high-speed dry ice particles S onto the reflective surface 11A for several hours to several tens of hours, so-called $CO_2$ snow cleaning. The dry ice particles sprayed on the reflective surface 11A may instantaneously expand the contaminants attached to the reflective surface 11A to separate the contaminants from the reflective surface 11A. In the first cleaning process S300, the first cleaning apparatus 150 is moved along the surface of the reflective surface 11A, and sprays dry ice particles S on the reflective surface 11A in a uniform amount per unit time. For example, the first cleaning process S300 may be performed entirely on the reflective surface 11A without taking into account the level of partial contamination of the reflective surface 11A. Through this process, relatively large contaminants P1 among the contaminants P1 and P2 attached to the reflective surface 11A may be removed. After the first cleaning process (S300) is performed, the operation (S100) of measuring the contamination level of the reflective surface 11A with the first measuring device 140 may be performed again. This process may be repeated until the contamination level of the reflective surface 11A is measured to be less than or equal to the reference value.

Figure 8:
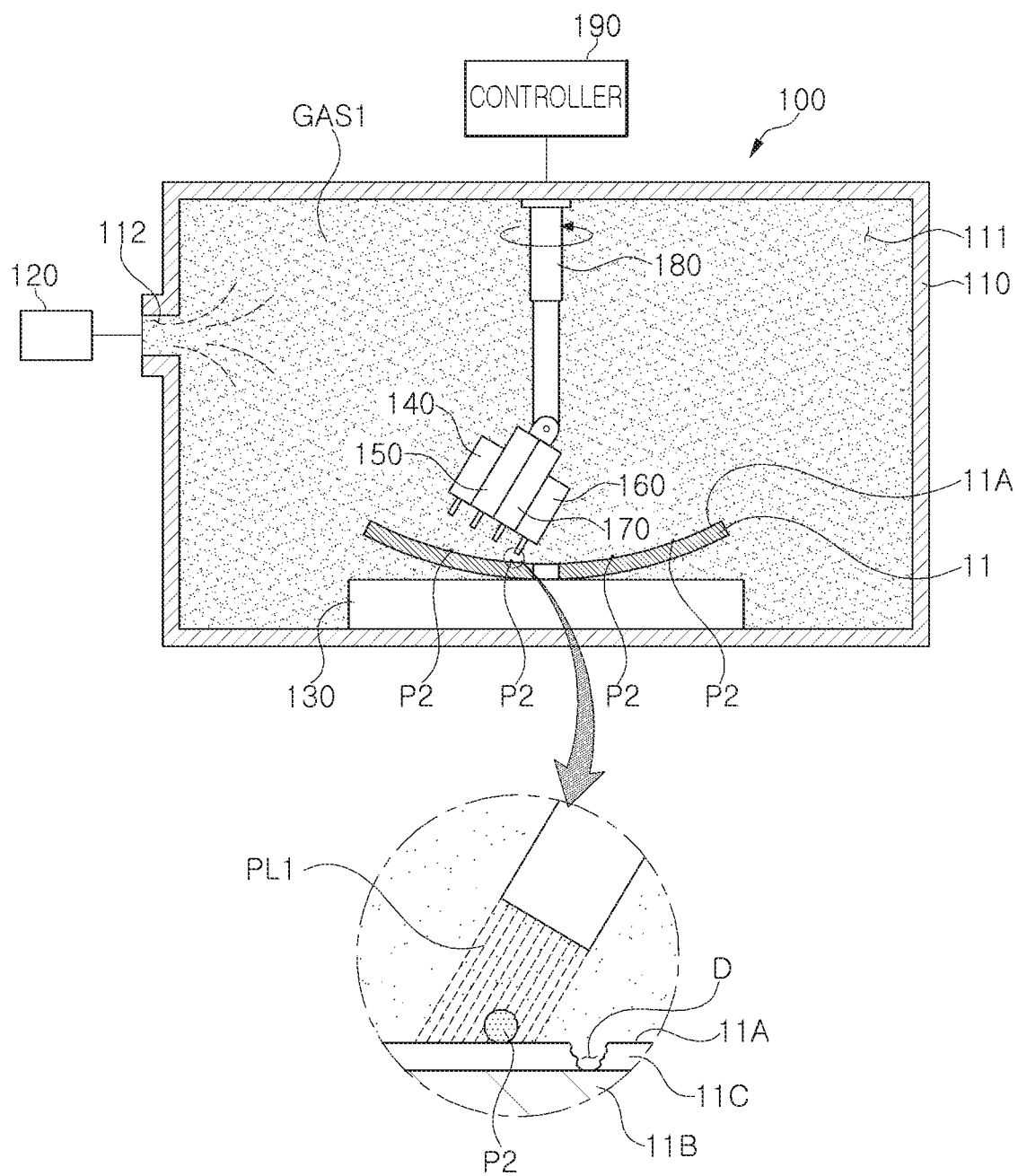
Figure 9:
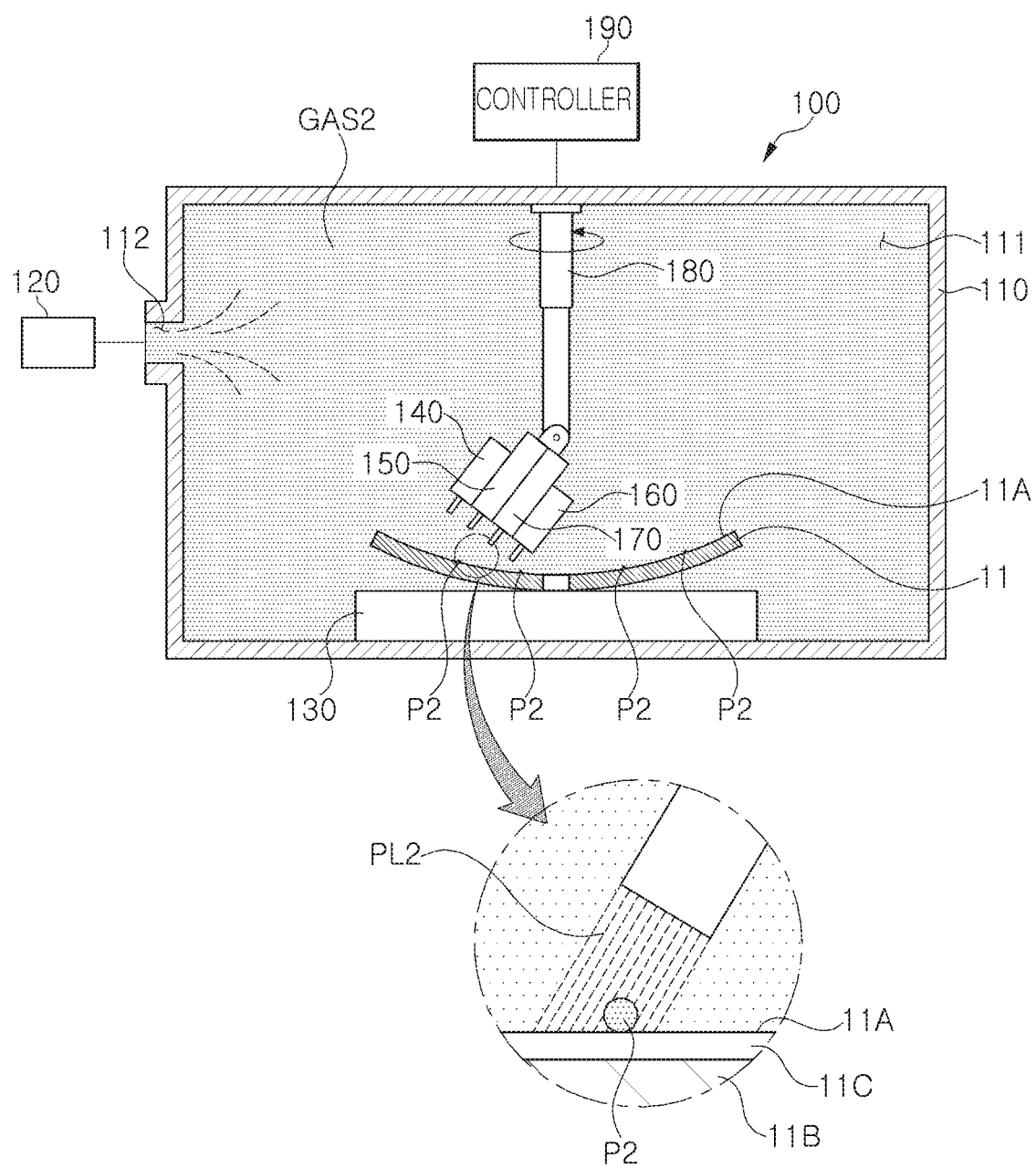

Referring to FIGS. 4 and 8, a second cleaning process (S400) is a process of removing the microcontaminants P2 attached to the reflective surface 11A. In the second cleaning process S400, chemical cleaning may be performed to remove microcontaminants P2 having a size smaller than the contaminants P1 removed in the first cleaning process. The microcontaminants P2 may be firmly adhered to the reflective surface 11A and remain on the reflective surface 11A even after the first cleaning process is performed. Referring to FIG. 5, in the second cleaning process, measuring the level of microcontamination of the reflective surface 11A with the second measuring device 160 (S410), measuring the level of damage to the reflective surface 11A (S420), and cleaning the reflective surface 11A with atmospheric plasma (S430) may be performed. Operations S410 to S430 may be performed sequentially, but inventive concepts are not limited thereto, and may be performed simultaneously according to an example embodiment. In an example embodiment, a case in which operations S410 to S430 are sequentially performed will be described as an example.

Referring to FIGS. 5 and 8, the operation (S410) of measuring the microcontamination level of the reflective surface 11A by the second measuring device 160 is an operation of measuring a microcontamination level of a contamination area to which the microcontaminants P2 are attached to the reflective surface 11A by using the second measuring device 160. The controller 190 may generate a microcontamination level map by matching the measured distribution of the contamination area to a location value. The operation (S420) of measuring the level of damage of the reflective surface 11A by the second measuring device 160 is an operation of measuring the area in which the reflective layer 11C constituting the reflective surface 11A is damaged. The controller 190 may measure the level of damage of the reflective surface 11A with the second measuring device 160, and may generate a damage level map by matching the measured damage value to the location value.

Referring to FIG. 8, in the operation of measuring the microcontamination level of the reflective surface 11A with the second measuring device 160 (S410), the second measuring device 160 is brought close to the reflective surface 11A, the atmospheric plasma (PL1) is radiated to the reflective surface 11A, and a chemical species detected on the reflective surface 11A is detected, thereby measuring the level of microcontamination of the reflective surface 11A. To this end, a first process gas GAS1 may be injected into the cleaning chamber 110. As the first process gas GAS1, a hydrogen-based gas or an argon-based gas may be used. When a hydrogen-based gas including a hydrogen radical is used as the first process gas GAS1, operations S410 to S430 may be simultaneously performed. For example, measurement by the second measuring device 160 and cleaning by the second cleaning apparatus 170 may be performed simultaneously, and there is no need to inject a separate second process gas in a subsequent process, which will be described later.

On the other hand, when an argon-based gas is used as the first process gas GAS1, only the microcontamination level of the reflective surface 11A by the second measuring device 160 may be measured, and in the subsequent process, it is necessary to inject a separate process gas necessary for cleaning, into the second cleaning apparatus 170. According to an example embodiment, an example in which an argon-based gas is used as the first process gas GAS1 will be described.

The microcontamination level of the reflective surface 11A may be measured by checking the type of chemical species detected through the second measuring device 160. For example, a region in which a substance, e.g., tin (Sn), included in the droplet is detected as a chemical species may be regarded as a region to which the microcontaminants P2 are attached. Also, a region in which a material included in the reflective layer 11C constituting the reflective surface 11A is detected as a chemical species may be regarded as an uncontaminated region. In addition, a region in which a material included in the body 11B below the reflective layer 11C is detected as a chemical species may be regarded as the reflective layer 11C of the reflective surface 11A is damaged Next, referring to FIGS. 5 and 9, atmospheric plasma cleaning (S430) may be performed on an area in which the microcontamination level exceeds a reference value, based on the generated microcontamination level map and the damage level map. To this end, second process gas GAS2 may be injected into the cleaning chamber 110. In an example embodiment, a hydrogen-based gas including a hydrogen radical may be used as the second process gas GAS2. The microcontaminants P2 not removed in the first cleaning process (S300) are strongly attached to the reflective surface 11A and are not easily removed by physical cleaning. Therefore, in the second cleaning process (S400), atmospheric plasma cleaning, which is chemical cleaning stronger than physical cleaning, may be performed using the second cleaning apparatus 170 to remove the microcontaminants P2.

Since atmospheric plasma cleaning is performed by radiating plasma (PL2) in a relatively significantly narrow range, a lot of time may be consumed for cleaning. In an example embodiment, the controller 190 may restrict how the atmospheric plasma cleaning is performed. For example, the controller 190 may restrict the atmospheric plasma cleaning so the atmospheric plasma cleaning is performed only in a region in which the contamination level exceeds a reference value by referring to the microcontamination level map.

In addition, since atmospheric plasma cleaning is performed by irradiating plasma (PL2) in a significantly narrow range, if the cleaning is performed in a case in which the reflective layer 11C constituting the reflective surface 11A of the collector 11 is damaged, permanent damage to the collector 11 may occur. Accordingly, the controller 190 may restrict how the atmospheric plasma cleaning is performed. For example the controller 190 may restrict the atmospheric plasma cleaning so the atmospheric plasma cleaning is performed only on the region excluding a region D in which the reflective layer 11C is damaged by referring to the previously generated damage level map.

Next, a case in which operations S410 to S430 of the second cleaning process S400 are simultaneously performed will be described.

When a hydrogen-based gas including a hydrogen radical is used as the first process gas GAS1, operations S410 to S430 may be simultaneously performed. For example, the operation of measuring the level of contamination and damage of the reflective surface 11A with the second measuring device 160 and the operation of cleaning the reflective surface 11A with the second cleaning apparatus 170 may be performed simultaneously.

The controller 190 may perform atmospheric plasma cleaning of the entire reflective surface 11A using the second cleaning apparatus 170 in a state in which the hydrogen-based first process gas GAS1 is injected into the cleaning chamber 110. The atmospheric plasma cleaning may be performed as the second cleaning apparatus 170 moves along the reflective surface 11A after the second cleaning apparatus 170 approaches the reflective surface 11A. The controller 190 may detect a chemical species emitted from the reflective surface 11A in the atmospheric plasma cleaning process, using the second measuring device 160, and measure the level of microcontamination and damage of the region in which plasma cleaning is performed. The controller 190 may increase the time during which atmospheric plasma cleaning is performed in an area having a relatively high level of microcontamination, thereby intensively cleaning an area having a high level of microcontamination. Also, when the damaged area D is detected in the reflective surface 11A, the controller 190 may stop the second cleaning process (S400) from being performed to limit and/or prevent damage to the collector 11.

As set forth above, according to an example embodiment, a method of cleaning a collector of an extreme ultraviolet light-source system, in which contaminants on a surface of the collector may be cleaned effectively by changing a cleaning process depending on the level of contamination on the surface of the collector.

One or more of the elements disclosed above may include or be implemented in processing circuitry such as hardware including logic circuits; a hardware/software combination such as a processor executing software; or a combination thereof. For example, the processing circuitry more specifically may include, but is not limited to, a central processing unit (CPU), an arithmetic logic unit (ALU), a digital signal processor, a microcomputer, a field programmable gate array (FPGA), a System-on-Chip (SoC), a programmable logic unit, a microprocessor, application-specific integrated circuit (ASIC), etc.

While example embodiments have been illustrated and described above, it will be apparent to those skilled in the art that modifications and variations could be made without departing from the scope of inventive concepts as defined by the appended claims.

What is claimed is:

1. A method of cleaning a collector of an extreme ultraviolet light source system, comprising:
   introducing the collector, separated from the extreme ultraviolet light source system, into a chamber of a cleaning apparatus, the cleaning apparatus including a controller;
   capturing an optical image of a reflective surface of the collector;
   measuring a contamination level of the reflective surface by comparing the optical image with a prestored standard image;
   performing a first cleaning process if the contamination level exceeds a preset first reference value, the first cleaning process including cleaning the reflective surface by spraying dry ice particles onto the reflective surface; and
   performing a second cleaning process if the contamination level is less than or equal to the preset first reference value, the second cleaning process including cleaning the reflective surface by radiating atmospheric plasma onto the reflective surface,
   wherein the second cleaning process includes,
      measuring a microcontamination level of the reflective surface and a damage level of the reflective surface,
      generating a microcontamination level map of the reflective surface and a damage level map of the reflective surface, based on the microcontamination level and the damage level, and
   cleaning by radiating the atmospheric plasma onto an area of the reflective surface in which the microcontamination level and the damage level exceed a preset second reference value and a present third reference value, respectively, based on the microcontamination level map and the damage level map, and
   wherein the controller is configured to control an operation of the cleaning apparatus such that the cleaning apparatus performs the first cleaning process if the contamination level exceeds the preset first reference value and the cleaning apparatus performs the second cleaning process if the contamination level is less than or equal to the preset first reference value.

2. The method of claim 1, wherein
   the second cleaning process is performed in response to the contamination level being less than or equal to the first preset reference value,
   the collector comprises a body and a reflective layer,
   the body includes a first material,
   the reflective layer is on a surface of the body to provide the reflective surface,
   the reflective layer includes a second material different from the first material, and
   the measuring a microcontamination level and a damage level of the reflective surface includes determining that a portion of the reflective surface is damaged if a chemical species of the first material is detected in the portion of the reflective surface.

3. The method of claim 1, wherein
   the second cleaning process is performed in response to the contamination level being less than or equal to the preset first reference value, and
   the measuring a microcontamination level and a damage level of the reflective surface further comprises supplying a gas containing argon into the chamber.

4. The method of claim 2, wherein the measuring a microcontamination level and a damage level of the reflective surface is performed by radiating the atmospheric plasma onto the portion of the reflective surface and detecting a chemical species emitted from the portion.

5. The method of claim 2, wherein the measuring a microcontamination level and a damage level of the reflective surface comprises determining that the portion is contaminated if the chemical species is tin (Sn).

6. The method of claim 1, wherein
the second cleaning process is performed in response to the contamination level being less than or equal to the preset first reference value, and
the cleaning by radiating the atmospheric plasma further comprises supplying a gas containing a hydrogen radical into the chamber.

7. A method of cleaning a collector of an extreme ultraviolet light source system, comprising:
inputting the collector separated from the extreme ultraviolet light source system into a chamber of a cleaning apparatus, the cleaning apparatus including a controller;
capturing an optical image of a reflective surface of the collector;
measuring a contamination level of the reflective surface by comparing the optical image with a pre-stored standard image;
performing a first cleaning operation if the contamination level exceeds a preset first reference value, the first cleaning operation including cleaning the reflective surface by spraying dry ice particles onto the reflective surface; and
performing a second cleaning operation if the contamination level is less than or equal to the preset first reference value, the second cleaning operation including cleaning the reflective surface by radiating atmospheric plasma onto the reflective surface and measuring a microcontamination level and a damage level of the reflective surface,
wherein the controller is configured to control an operation of the cleaning apparatus such that the cleaning apparatus performs the first cleaning operation if the contamination levels exceeds the preset first reference value and the cleaning apparatus performs the second cleaning operation if the contamination level is less than or equal to the preset first reference value.

8. The method of claim 7, further comprising:
remeasuring the contamination level of the reflective surface after the performing the first cleaning operation.

9. The method of claim 8, wherein the performing the first cleaning operation and the remeasuring the contamination level of the reflective surface are repeatedly performed until the contamination level is less than or equal to the preset first reference value.

10. The method of claim 7, wherein
the second cleaning operation is performed in response to the contamination level being less than or equal to the preset first reference value,
the second cleaning operation further comprises supplying a gas containing a hydrogen radical into the chamber.

11. The method of claim 7, wherein
the collector comprises a body and a reflective layer,
the body includes a first material,
the reflective layer is on a surface of the body to provide the reflective surface,
the reflective layer includes a second material different from the first material, and
the second cleaning operation comprises determining that the reflective surface is damaged if a chemical species of the first material is detected on the reflective surface.

12. The method of claim 11, wherein
the second cleaning operation includes stopping radiation of the atmospheric plasma if the reflective surface is determined to be damaged.

13. The method of claim 11, wherein the second cleaning operation comprises determining that the reflective surface is not contaminated if a chemical species of the second material is detected on the reflective surface.

14. The method of claim 7, wherein
the extreme ultraviolet light source system comprises a light source chamber, a droplet supply unit, and a laser light source,
the collector is in the light source chamber,
the droplet supply unit is on a sidewall of the chamber,
the droplet supply unit is aligned to discharge a droplet along a path traversing an upper portion of the collector,
the second cleaning operation is performed in response to the contamination level being less than or equal to the preset first reference value,
the laser light source is configured to irradiate a laser beam to the droplet, on the path, and
the second cleaning operation is performed by measuring the microcontamination level by detecting a spectrum of a material constituting the droplet in a spectral image of the reflective surface.

15. The method of claim 14, wherein the droplet includes tin (Sn), and
the second cleaning operation includes determining that the collector is contaminated if a spectrum of the tin is detected in the spectral image of the reflective surface.

16. A method of cleaning a collector of an extreme ultraviolet light source system, comprising:
introducing the collector, separated from the extreme ultraviolet light source system, into a chamber of a cleaning apparatus, the cleaning apparatus including a controller;
capturing an optical image of a reflective surface of the collector using a first measuring device;
measuring a contamination level of the reflective surface by comparing the optical image with a pre-stored standard image;
performing a first cleaning operation if the contamination level exceeds a preset first reference value, the first cleaning operation including physically cleaning the reflective surface by spraying dry ice particles onto the reflective surface using a first cleaning apparatus; and
performing a second cleaning operation if the contamination level is less than or equal to the preset first reference value, the second cleaning operation including chemically cleaning the reflective surface by radiating atmospheric plasma onto the reflective surface using a second cleaning apparatus and measuring a microcontamination level of the reflective surface and a damage level of the reflective surface using a second measuring device,
wherein the controller is configured to control an operation of the cleaning apparatus such that the cleaning apparatus performs the first cleaning operation if the contamination level exceeds the preset first reference value and the cleaning apparatus performs the second cleaning operation if the contamination level is less than or equal to the preset first reference value.

17. The method of claim 16, wherein
the second cleaning process is performed in response to the contamination level being less than or equal to the preset first reference value,
in the second cleaning operation, the second measuring device moves along the reflective surface and detects a chemical species in each region of the reflective surface, and the second cleaning operation includes determining that the reflective surface is contaminated if the second measuring device detects tin (Sn) as the chemical species in a corresponding region of the reflective surface.

18. The method of claim 17, wherein the second cleaning operation includes determining that the reflective surface is not contaminated if the second measuring device detects a material constituting a surface of the reflective surface in a corresponding region of the reflective surface.

19. The method of claim 16, wherein the second measuring device includes at least one of an optical emission spectrometer, an optical absorption spectrometer, and a laser induced fluorescence detector.

20. The method of claim 19, wherein the second measuring device further comprises a gas detector.

* * * * *